United States Patent [19]
Goodman

[11] Patent Number: 5,853,004
[45] Date of Patent: Dec. 29, 1998

[54] PHARYNGEAL BULB AIRWAY

[76] Inventor: Evan J. Goodman, 3725 Severn Rd., Cleveland Heights, Ohio 44118

[21] Appl. No.: 867,187

[22] Filed: Jun. 2, 1997

[51] Int. Cl.⁶ .................................................... A61M 16/00
[52] U.S. Cl. ................................. 128/207.15; 128/207.14
[58] Field of Search ........................ 128/200.26, 200.24, 128/207.14, 207.15, 911, 912, DIG. 26; 604/96

[56] References Cited

U.S. PATENT DOCUMENTS

| | | |
|---|---|---|
| 2,099,127 | 11/1937 | Leech . |
| 3,470,876 | 10/1969 | Barchilon . |
| 3,774,596 | 11/1973 | Cook . |
| 3,968,800 | 7/1976 | Vilasi . |
| 4,141,364 | 2/1979 | Schultze . |
| 4,150,676 | 4/1979 | Jackson . |
| 4,211,234 | 7/1980 | Fisher . |
| 4,235,239 | 11/1980 | Elam . |
| 4,509,514 | 4/1985 | Brain . |
| 4,622,965 | 11/1986 | Teeple . |
| 4,781,704 | 11/1988 | Potter . |
| 4,795,458 | 1/1989 | Regan . |
| 4,840,172 | 6/1989 | Augustine et al. . |
| 4,852,568 | 8/1989 | Kensey . |
| 4,919,126 | 4/1990 | Baildon . |
| 4,995,388 | 2/1991 | Brain . |
| 5,061,274 | 10/1991 | Kensey . |
| 5,147,370 | 9/1992 | McNamara et al. . |
| 5,217,005 | 6/1993 | Weinstein . |
| 5,303,697 | 4/1994 | Brain . |
| 5,323,771 | 6/1994 | Fisher et al. . |
| 5,429,127 | 7/1995 | Kolobow . |
| 5,496,332 | 3/1996 | Sierra et al. . |
| 5,513,660 | 5/1996 | Simon et al. . |
| 5,682,880 | 11/1997 | Brain . |

Primary Examiner—Mickey Yu
Assistant Examiner—Dinh X. Nguyen
Attorney, Agent, or Firm—Howard M. Cohn

[57] ABSTRACT

A pharyngeal bulb airway adapted to be placed in the airway of a person who is otherwise incapable of self sustained breathing, consists of a pliable, hollow dome-like-shaped bulb connected to a breathing tube. Insertion of the pharyngeal bulb airway breathing device into the airway of a person is facilitated by compressing the bulb to reduce its size, and by the use of a flexible rod or wire to maintain the reduced size until the breathing device is properly positioned. The flexible rod or wire is threaded through holes formed within the dome-like-shaped bulb after the bulb has been collapsed. When the wire is removed from the holes, the bulb resumes its normal dome-like shape. The bulb is preferably adapted to be placed in the pharynx with the holes facing in the direction of the epiglottis.

15 Claims, 2 Drawing Sheets

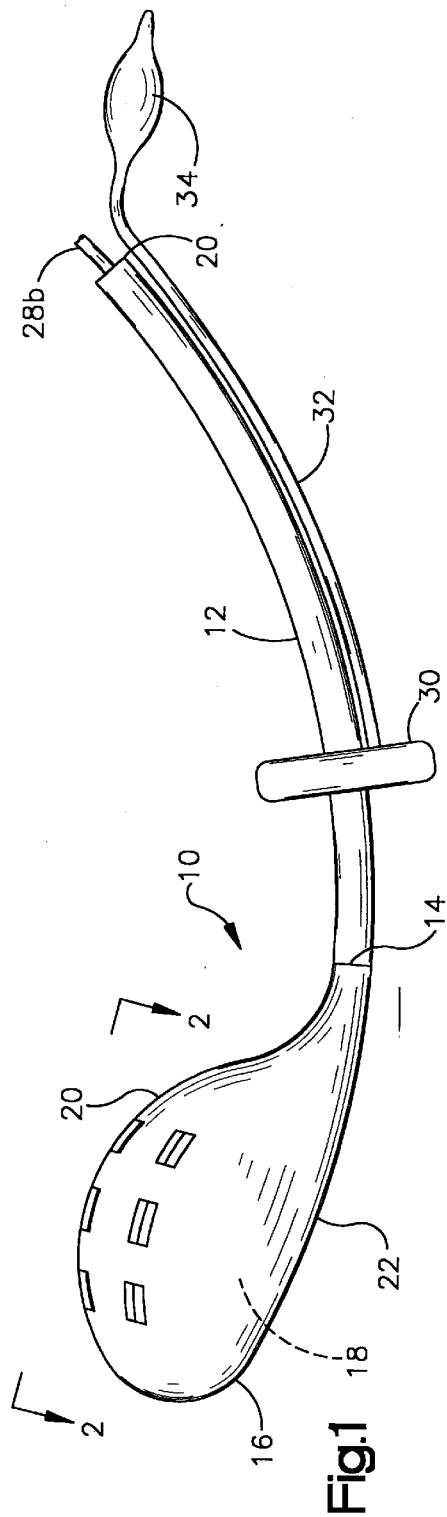
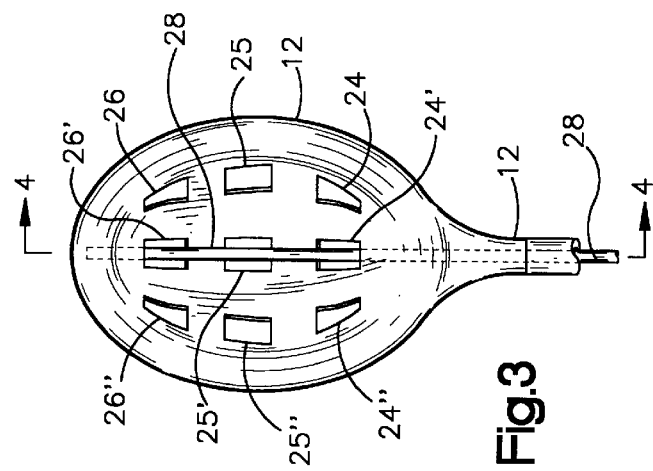
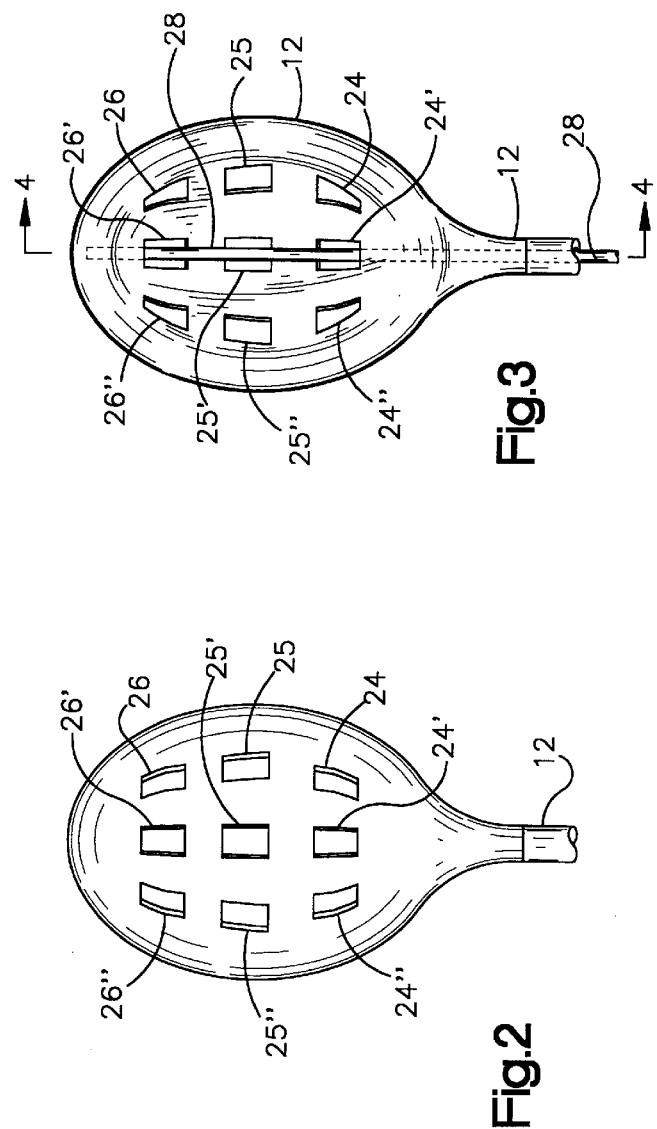

PHARYNGEAL BULB AIRWAY

FIELD OF THE INVENTION

This invention relates to the field of artificial breathing devices for permitting and assisting ventilation of persons who are unconscious or who are, for certain reasons, unable to breathe on their own. More specifically, the invention relates to such devices that are designed to be placed in the pharynx of such a person to permit or to assist the person in the basic function of breathing.

BACKGROUND OF THE INVENTION

A number of artificial devices are available for assistive breathing of persons who have suffered temporary or permanent loss of all or part of their pulmonary functions. A basic pharyngeal bulb airway also known as stylets is a face mask which is adapted to fit over and conform to the mouth and nasal openings of the person. It is connected by tubing to an oxygen supply, a respirator or other artificial breathing devices.

A number of other devices are available for insertion directly into the airway of the person for assistive breathing. One device used in the normal practice of anesthesia is referred to as an endotracheal tube. This tube, which is constructed of soft rubber or plastic, terminates in an inflatable cuff which is inserted into the trachea and is then inflated to form a relatively airtight seal with the walls of the trachea. The tube generally must be inserted through the larynx into the trachea using a laryngoscope to guide the tube through the larynx. Intubation, or insertion of the tube, must be done with care to avoid damage to the larynx. Also accidental insertion of the tube into the esophagus or into one of the bronchial tubes must be avoided.

Another type of pharyngeal bulb airway, referred to as a laryngeal mask, is adapted to be inserted into the pharynx of a person, thereby avoiding the problems associated with intubation into the trachea. The laryngeal mask is shown and described in the following U.S. Pat. Nos.: 4,509,514; 4,995,388; and 5,303,697, the subject matter of which are intended to be incorporated by reference in their entireties. The laryngeal mask is attached to an airway tube and has an inflatable elliptical collar. This collar is designed when inflated to form a seal to the inlet to the larynx. The laryngeal mask requires the skills and protocols which are only available in hospitals and does not lend itself to use by paramedics and emergency medical personnel in the field. Furthermore, due to the contour of the airway, the laryngeal mask is often inserted into the airway of the person with the interior of the mask facing backward, after which the mask is then rotated 180° into proper position. This method of insertion increases the risk of damage or trauma to the windpipe and surrounding tissue as well as additional stress on the patient during rotation.

OBJECTS AND SUMMARY OF THE INVENTION

It is an object of the present invention to provide a pharyngeal bulb airway which obviates the problems of the prior art and can be as defined in one or more of the appended claims and, as such, has the capability of being constructed to accomplish one or more of the following subsidiary objects.

Another object of the present invention is to provide a pharyngeal bulb airway which can be quickly and easily inserted into the pharynx of a person in emergency situations without the use of a laryngoscope.

Yet another object of the present invention is to provide a pharyngeal bulb airway which can be inserted into a person's airway without the need to rotate the device into position after insertion.

Still another object of the present invention is to provide a pharyngeal bulb airway which can be positioned and used in the pharynx of a patient without causing undue cardiovascular distress on the patient.

Yet another object of the present invention is a pharyngeal bulb airway, the use of which results in a low incidence of sore or irritated throat following its use on the patient.

Another object of the present invention is a pharyngeal bulb airway which discourages air from entering the esophagus of a patient without the need to completely close the esophagus.

These and other objects and advantages of the invention which will become apparent upon a full understanding of this invention are achieved in the manner to be hereinafter described in greater detail.

The present invention relates to an assistive breathing device, referred to as a pharyngeal bulb airway herein, adapted to be positioned in the airway of a person who is in need of assistive breathing. The pharyngeal bulb airway comprises a hollow bulb also known as balloon and cuff capable of being collapsed by compression for ease of insertion into the airway of the person. The device then returns to its normal, uncompressed shape when properly positioned in the airway. The bulb includes a normally dome-like-shaped surface constructed of a pliant material, such as plastic or rubber, capable of being deformed when compressed to collapse or flatten the bulb and facilitate insertion or intubation within a patient's airway. The bulb includes a normally dome-like-shaped frontal surface having a plurality of discrete openings on its surface. The dome-like-shaped frontal surface is generally oval in cross-sectional shape. The bulb is connected and in fluid communication with a tube that extends out through the mouth of the person. A flexible rod or flexible wire extends along the breathing tube, either on the inside or the exterior thereof with one end of the flexible rod or flexible wire terminating in the bulb. The flexible rod or flexible wire passes out of the bulb through a first of the openings in the surface of the dome-like, and back into the bulb through a second hole. The flexible rod or flexible wire is inserted into the bulb while the bulb is collapsed, and prevents the bulb from returning to its dome-like shape until the bulb is in position in the airway. Then, by withdrawing the rod from the bulb, the bulb is allowed to return to its normal dome-like shape. The breathing device preferably includes an inflatable, donut-shaped balloon surrounding the tube intermediate its ends. When the device is properly positioned in the pharynx, the donut-shaped balloon is inflated into contact with the wall of the airway to form a relatively airtight seal, thereby compelling ventilated air to pass through the bulb and tube between the lungs and the respirator to the atmosphere.

In another embodiment of the present invention, an aspiration device, also known as a pharyngeal bulb airway herein, adapted for insertion into the airway of an unconscious person comprises, in combination, a) a breathing tube having a first end adapted to be vented to the atmosphere or connected to a suitable life-sustaining apparatus, b) a hollow flexible, generally oval bulb connected to the second end of the tube in open communication therewith, the oval bulb having one generally planar surface and a dome-like-shaped surface opposite the planar surface, the dome-like-shaped surface containing a plurality of discrete holes and adapted to be manipulated toward the generally planar surface to collapse the bulb, and c) a flexible rod extending the length of the breathing tube from the first end to the second end and into the bulb. The flexible rod extends out of the bulb through a first of the holes and back into the bulb through a second of the holes while the bulb is collapsed whereby the bulb is maintained generally collapsed during insertion into the airway. The pharyngeal bulb airway typically includes a pneumatically inflatable donut shaped balloon surrounding the breathing tube intermediate its two ends. The balloon serves to minimize the amount of air which escapes along the airway around the outside of the tube. The pharyngeal bulb airway includes structure to enable the flexible rod or wire to be removed from the bulb and permit the bulb to assume its normal dome-like shape when the device is properly positioned in a patient's airway. The rod or wire is typically a plastisol-covered metal rod or a plastic monofiliment. The bulb and the tube are typically made from rubber or plastic, preferably a rubber such as silicone rubber. The pharyngeal bulb airway is adapted to be positioned in the pharynx of the person whereby the dome-like-shaped surface is positioned against the epiglottis to permit aspirated air to pass through the holes into the bulb and out the breathing tube. Generally, holes in the shape of longitudinal slots extending along the major axis of the oval have been found to be satisfactory.

BRIEF DESCRIPTION OF THE DRAWINGS

The structure, operation, and advantages of the presently preferred embodiment of the invention will become further apparent upon consideration of the following description taken in conjunction with the accompanying drawings, wherein:

FIG. 1 is a perspective view of the pharyngeal bulb airway of the present invention showing a bulb joined to breathing tube;

FIG. 2 is a view of the bulb taken along line 2—2 of FIG. 1;

FIG. 3 is a view of the bulb while in the collapsed position;

DETAILED DESCRIPTION OF THE INVENTION

Figure 4:
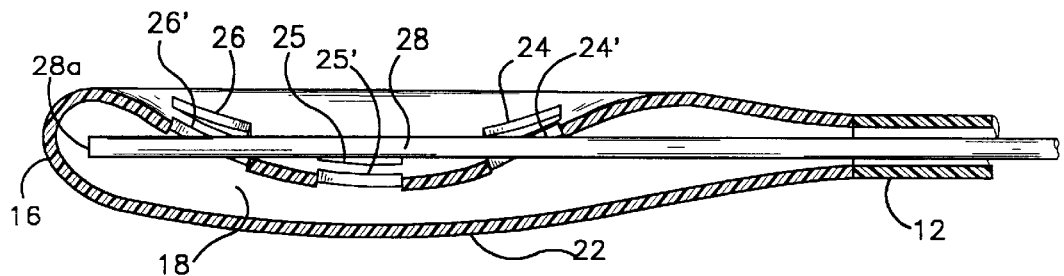
FIG. 4 is a view taken along lines 4—4 of FIG. 3.

Referring now to the drawings, FIG. 1 is a schematic illustration of an aspiration device or pharyngeal bulb airway 10 of the present invention. The pharyngeal bulb airway 10 is composed of a flexible breathing tube 12 with the first end 14 butt welded or otherwise joined to a hollow bulb 16 having a hollow interior 18. The second end 20 of the tube 12 is preferably adapted to be vented to the atmosphere or connected to a ventilating apparatus as needed.

The hollow bulb 16 is generally oval in shape and comprises a dome-like-shaped top surface 20 and a relatively planar bottom surface 22. The top surface 20 contains a plurality of discrete holes or openings 24, 24', 24", 25, 25', 25", 26, 26' and 26" extending therethrough. Preferably, the bulb 16 is made of a molded plastic or rubber and is semi-rigid and is sufficiently pliable that it can be compressed or collapsed, as shown in FIGS. 3 and 4, by pressing the top surface 20 towards the bottom surface 22, such as between the thumb and index finger of a user, to reduce its overall thickness by at least about 50%, and preferably more. When the digital pressure is released, the bulb 16 has sufficient elastic memory for its top surface 20 to return to its normal dome-like-shape, as shown in FIG. 1. Unlike prior art aspiration devices, such as those described in the aforementioned patents, the bulb 16 is not inflatable.

The purpose of compressing or collapsing the dome-like-shaped bulb 16 is to reduce its bulk and elevational thickness to thereby facilitating its insertion into the throat of an unconscious person. In accordance with the invention, a flexible rod or wire 28 extends within and along the length of tube 12 and into the bulb 16. The first end 28a of the flexible rod or wire 28 can be threaded out of the bulb 16 through a first hole 24' and then back into the bulb through a second hole 26', as shown in FIGS. 3 and 4, while the bulb is manually compressed. While the rod or wire 28 is described as extending through the holes 24' and 26', it is also within the terms of the invention to insert the rod or wire through other of the holes. Although the flexible rod or wire 28 is bendable, it is sufficiently rigid in the lateral direction to prevent the compressed bulb 16 from resuming its normal dome-like shape while the rod or wire 28 extends through the holes 24' and 26'. Once the breathing device 10 is positioned in the proper location in the pharynx, the rod or wire 28 is withdrawn from the holes 24' and 26' which causes the bulb 16 to return to its normal size and shape, as shown in FIG. 1. The withdrawal of the rod or wire 28 from the holes 24' and 26' of bulb 16 is can be done manually or mechanically by pulling the wire from its end 28b so that the wire is completely removed from the open end of the tube 12. It is also within the terms of the invention to remove the wire 28 from only one of the openings, i.e. 26', and leave the wire in the bulb 16. Although the rod or wire 28 is shown as extending along the interior of the tube 12 into the bulb interior 18, it should be understood that the rod or wire can be disposed within a special passageway (not shown) extending along the length of the tube with the first end 28a of the rod or wire extending into the bulb 16 as previously described. The flexible rod or wire 28 preferably is constructed of a plastisol coated, stainless steel or is a plastic monofilament having sufficient lateral strength to resist lateral deflecting when subject to the pressure exerted by the collapsed bulb 16.

Figure 5:
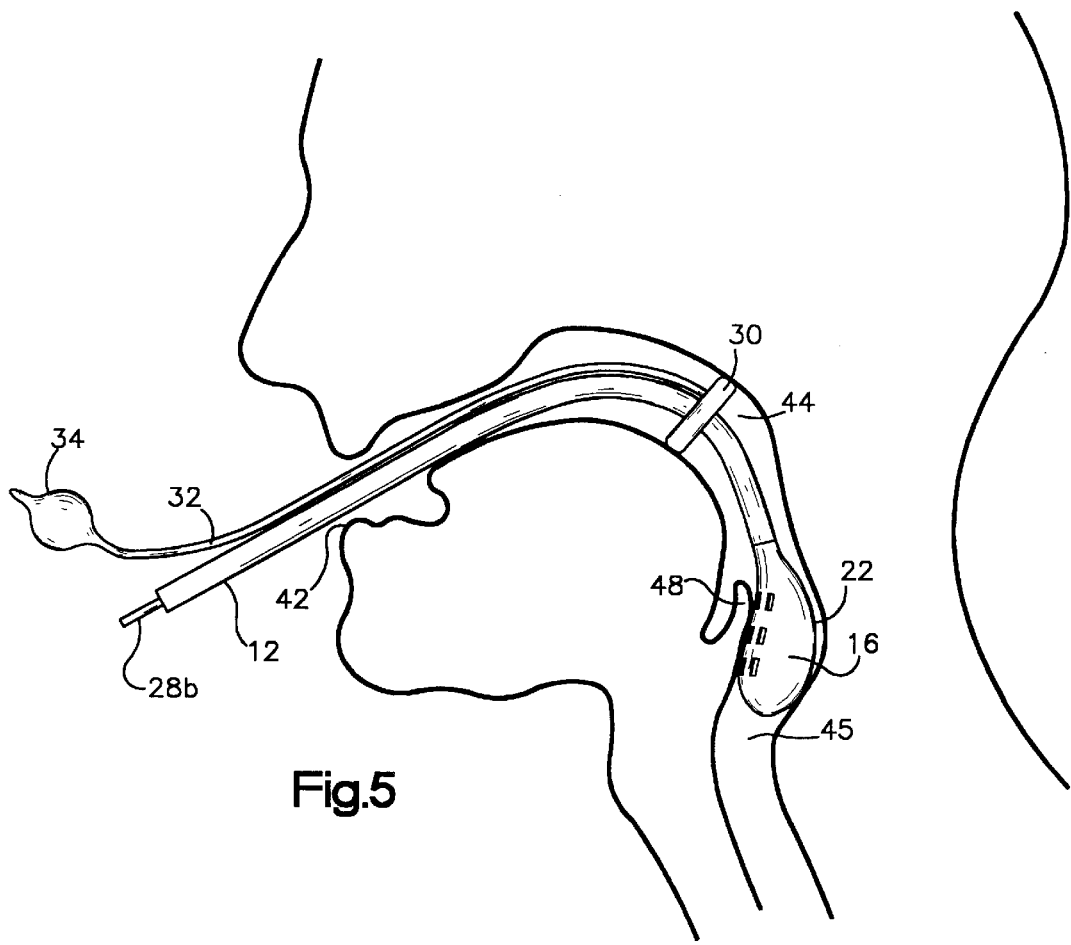
FIG. 5 is an elevational diagram of the head and neck of a person with the pharyngeal bulb airway of the present invention properly positioned in the airway.

An inflatable, donut-shaped, rubber balloon 30 surrounds the tube 12 to provide a closure in the patient's airway whereby the air is aspirated through the bulb 16 and tube 12 rather than around the outside of the tube. The donut-shaped balloon 30 is typically connected by an inflation tube 32 to a pilot balloon 34 which is attached to a syringe (not shown), as shown in FIG. 1. When the pharyngeal bulb airway 10 is properly positioned within a patient's airway, as shown in FIG. 5, the syringe directs air into the pilot balloon 34 and the donut-shaped balloon 30 to inflate balloon 30 until it makes firm contact with the wall of the patient's throat. In this manner, air is expelled from the patient's lungs through the multiplicity of discrete holes or openings 24, 24', 24", 25, 25', 25", 26, 26' and 26" in the bulb 16 and then through the tube 12 instead of around the outside of the tube. In like manner, incoming air enters the tube 12 and into the bulb 16 from where it passes out through the holes of discrete holes or openings 24, 24', 24", 25, 25', 25", 26, 26' and 26" and then into the lungs.

To insert the pharyngeal bulb airway 10 into a patient, the donut-shaped balloon 30 is fully deflated, and the bulb 16 is manually compressed so that the dome-like-shaped top surface 20 is collapsed into contact or near contact with the bottom surface 22 so that the height of the bulb 16 is reduced from its normal dimension to about 50% or less of that dimension. Typically the normal height of the bulb 16 is about 25 mm, and the reduced height is less than about 15 mm. The bulb 16 is maintained in the collapsed condition by the flexible rod or wire 28 which is threaded through two of the holes, i.e., 24' and 26', in the bulb. The portion of the collapsed dome-like-shaped top surface 20 between the two holes 24' and 26' can press against the rod or wire 28, as shown in FIG. 4, but is prevented from returning to its normal dome-like-like shape by the rod or wire 28. The bulb 16 is then inserted through the mouth 42 of the patient and into the throat 44, as shown in FIG. 5, until the bulb is positioned in the pharynx 46 with the holes facing the epiglottis 48 and the flat bottom surface 22 facing the back of the throat. When the pharyngeal bulb airway 10 is in place, the rod or wire 28 is withdrawn whereupon the dome-like-shaped top 20 resumes its normal shape, as shown in FIG. 5, so that the top 20 of the bulb 16 is in contact with the epiglottis 48. The donut-shaped balloon 30 is pneumatically inflated to prevent the passage of air around the outside of the tube. Subsequent removal of the pharyngeal bulb airway 10 from the throat can readily be carried out by deflating the donut-shaped balloon 30 without the need to collapse the bulb 16.

As previously stated, the bulb 16 is generally oval in its cross-sectional shape. The cross-sectional dimensions of the bulb can be approximately 40 mm. by 60 mm., although the bulbs can be made in a variety of sizes for use on infants, children, and adults. The bulb 16 is of a sufficient size to preclude stress and irritation caused by the inadvertent intubation into the esophagus or the bronchial tubes.

The pharyngeal bulb airway 10 is relatively inexpensive to produce and is adapted for disposable use. It can also be made of a material which can readily be sterilized for reuse if desired.

While the invention has been described in combination with embodiments thereof, it is evident that many alternatives, modifications, and variations will be apparent to those skilled in the art in light of the foregoing teachings. Accordingly, the invention is intended to embrace all such alternatives, modifications and variations as fall within the spirit and scope of the appended claims.

I claim:

1. A pharyngeal bulb airway adapted to be positioned in the airway of a patient, the device comprising:

a breathing tube adapted to extend out through the mouth of a patient;

a hollow bulb adapted to be inserted within the throat of the patient being connected to the breathing tube, the hollow bulb being constructed of a pliant material capable of allowing the hollow bulb to be either expanded in a normal shape or compressed into a collapsed condition; and a flexible rod or wire extending along the breathing tube and into the bulb and being releasably attached to the bulb to either selectively retain the bulb in the collapsed condition or to allow the bulb to resume its normal shape.

2. The pharyngeal bulb airway according to claim 1 wherein the hollow bulb further includes a normal dome-like shape top surface with a plurality of openings extending therethrough and a relatively planar bottom surface whereby the flexible rod or wire can be inserted through the openings to retain the bulb in the collapsed condition and withdrawn from the openings to allow the bulb to resume its normal dome-like shape.

3. The pharyngeal bulb airway according to claim 2 wherein the bulb is generally oval in cross section.

4. The pharyngeal bulb airway according to claim 2 wherein the flexible rod or wire extends through the interior of the breathing tube and into the hollow bulb.

5. The pharyngeal bulb airway according to claim 4 wherein the flexible rod or wire has a first end and a second end, the first end extending into two of the plurality of openings in the bulb and the second end projecting out of the breathing tube to enable the withdraw of the first end of the wire from at least one of the openings in the bulb.

6. The pharyngeal bulb airway according to claim 5 wherein the wire can be withdrawn completely from the interior of the breathing tube.

7. The pharyngeal bulb airway according to claim 1 further including a pneumatically inflatable balloon surrounding the breathing tube intermediate ends of the tube serving to make a relatively airtight seal with the wall of the airway to prevent air from escaping around the outside of the tube.

8. A pharyngeal bulb airway adapted for insertion into the airway of an unconscious person and comprising, in combination, a) a breathing tube having a first end adapted to be vented to the atmosphere or connected to suitable life-sustaining apparatus and a second end;

b) a hollow, flexible, generally oval bulb connected to the second end of the tube in open communication therewith, the bulb having a generally planar surface and a domelike-shaped surface opposite the planar surface, the dome-like-shaped surface containing a plurality of discrete openings, the dome-like-shaped surface adapted to be manipulated toward the planar surface to collapse the bulb for ease of insertion of the device into the airway, and c) a flexible rod or wire extending the length of the breathing tube from the first end to the second end and into the bulb, the flexible rod extending out of the bulb through one of the openings in the dome-like shaped surface and back into the bulb through a second of the openings whereby the bulb is maintained in a generally collapsed condition during insertion of the device into the airway.

9. The pharyngeal bulb airway according to claim 8 further including a pneumatically inflatable balloon surrounding the breathing tube intermediate its ends and being inflatable to minimize the amount of aspirated air which escapes around the outside of the tube.

10. The pharyngeal bulb airway according to claim 8 further including means to remove the flexible rod or wire from the openings in the bulb to permit the bulb to assume its normal dome-like shape.

11. The pharyngeal bulb airway according to claim 8 adapted to be positioned in the pharynx of the patient whereby the dome-like-shaped surface is positioned against the epiglottis while permitting aspirated air to pass through the openings into the bulb and out of the breathing tube.

12. The pharyngeal bulb airway according to claim 8 wherein the flexible rod or wire is selected from the group consisting a plastisol coated metal and a plastic monofilament.

13. The pharyngeal bulb airway according to claim 8 wherein the hollow oval bulb comprises molded rubber or molded plastic.

14. The pharyngeal bulb airway according to claim 13 wherein the bulb is composed of silicone rubber.

15. The pharyngeal bulb airway according to claim 8 wherein the openings are generally longitudinal slots extending along a longitudinal axis through the center of the oval bulb.

* * * * *